United States Patent
Nagorny et al.

(10) Patent No.: US 9,662,469 B2
(45) Date of Patent: May 30, 2017

(54) METHOD AND APPARATUS FOR BACKSPILL PREVENTION

(75) Inventors: Aleksandr Nagorny, Canoga Park, CA (US); David Sears, Woodland Hills, CA (US)

(73) Assignee: RedMed Limited, Bella Vista (AU)

(*) Notice: Subject to any disclaimer, the term of this patent is extended or adjusted under 35 U.S.C. 154(b) by 877 days.

(21) Appl. No.: 13/572,036

(22) Filed: Aug. 10, 2012

(65) Prior Publication Data

US 2012/0304989 A1 Dec. 6, 2012

Related U.S. Application Data

(62) Division of application No. 12/285,342, filed on Oct. 2, 2008, now Pat. No. 8,261,741.

(60) Provisional application No. 60/996,159, filed on Nov. 5, 2007.

(51) Int. Cl.
| | | |
|---|---|---|
| *A61M 11/00* | (2006.01) | |
| *A61M 16/16* | (2006.01) | |
| *A61M 16/00* | (2006.01) | |

(52) U.S. Cl.
CPC .......... *A61M 16/16* (2013.01); *A61M 16/161* (2014.02); *A61M 16/164* (2014.02); *A61M 16/0066* (2013.01); *A61M 2205/215* (2013.01)

(58) Field of Classification Search
CPC .......... A61M 16/0051; A61M 16/0003; A61M 16/16; A61M 2205/3334; A61M 16/0066; A61M 2205/215; A61M 16/161; A61M 16/164

USPC ........... 128/204.19, 202.22, 203.17, 203.26, 128/203.27, 204.18, 205.24
See application file for complete search history.

(56) References Cited

U.S. PATENT DOCUMENTS

| | | | |
|---|---|---|---|
| 4,538,129 A | 8/1985 | Fisher | |
| 6,000,417 A | 12/1999 | Jacobs | |
| 6,068,010 A | 5/2000 | Reinicke | |
| 6,182,657 B1 * | 2/2001 | Brydon et al. | 128/205.24 |
| 6,253,789 B1 | 7/2001 | Krimmer et al. | |
| 6,530,558 B1 | 3/2003 | Schulz | |
| 6,968,842 B1 * | 11/2005 | Truschel | A61M 16/00 128/204.18 |
| 8,701,662 B2 * | 4/2014 | Pujol et al. | 128/204.14 |
| 8,997,740 B2 * | 4/2015 | Pujol et al. | 128/205.24 |
| 2003/0127096 A1 * | 7/2003 | McAuliffe et al. | 128/204.18 |
| 2004/0060559 A1 * | 4/2004 | Virr et al. | 128/204.14 |
| 2007/0132117 A1 * | 6/2007 | Pujol et al. | 261/119.1 |
| 2009/0114221 A1 | 5/2009 | Nagorny et al. | |
| 2010/0071692 A1 * | 3/2010 | Porges | 128/203.16 |

* cited by examiner

*Primary Examiner* — Steven Douglas
(74) *Attorney, Agent, or Firm* — Nixon & Vanderhye P.C.

(57) ABSTRACT

A backspill prevention apparatus prevents water from a humidifier portion of a positive airway pressure (PAP) device from reaching a blower motor of a PAP device. The backspill prevention apparatus can include a variety of different devices, and is placed somewhere along an air passageway between a blower motor and a humidifier portion of a PAP device.

26 Claims, 15 Drawing Sheets

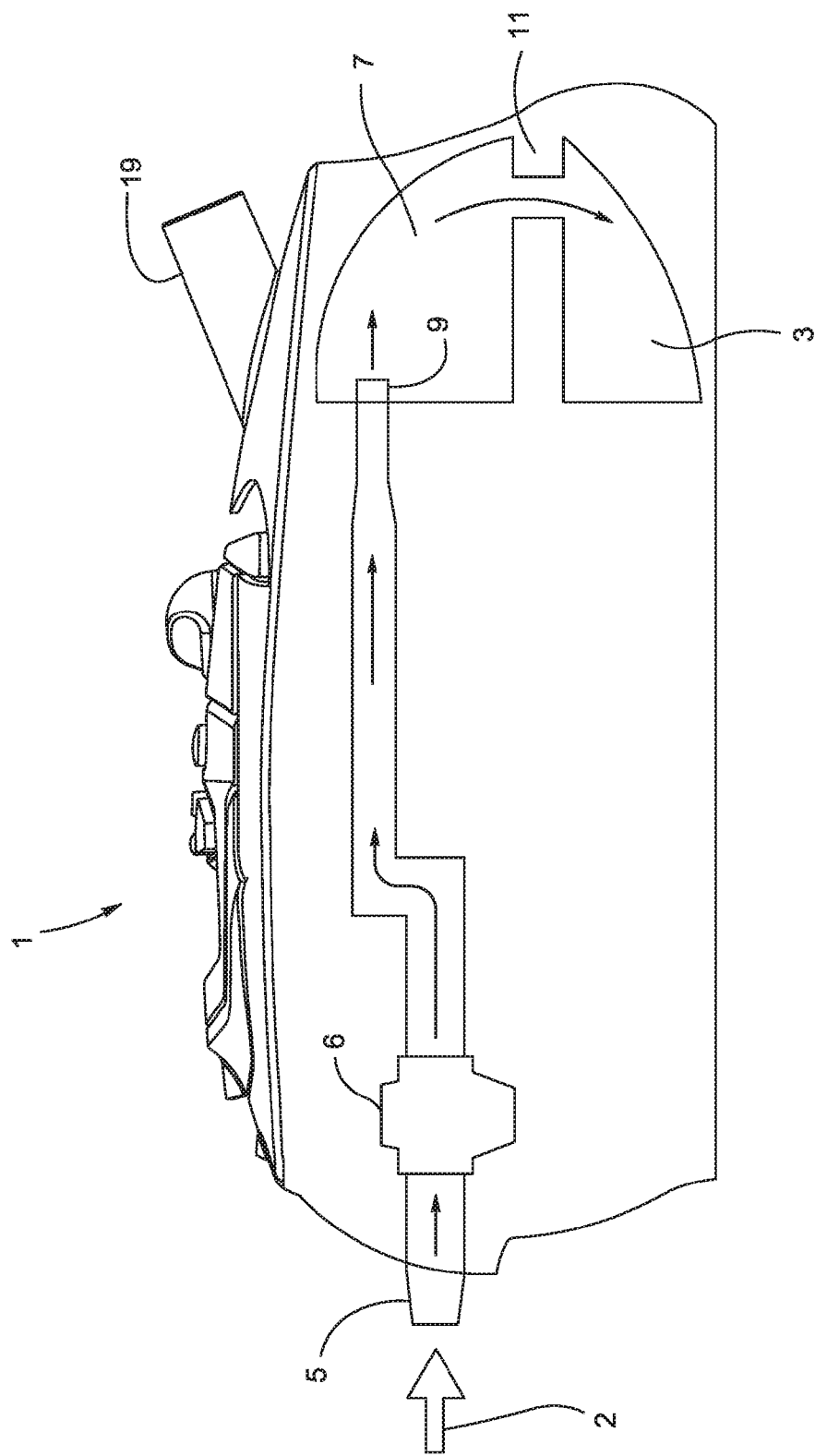

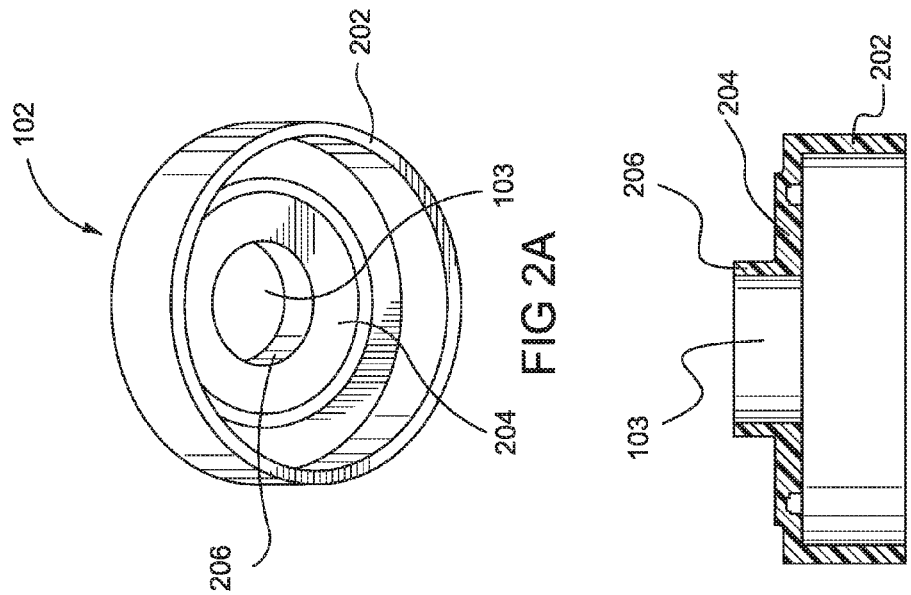
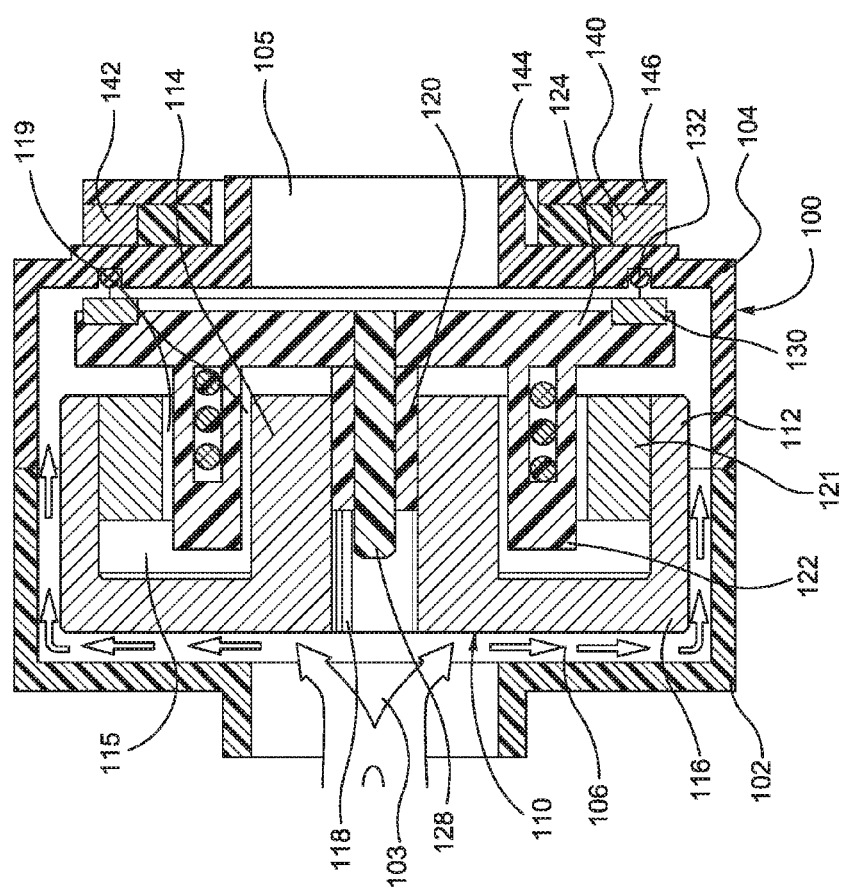
FIG. 1D

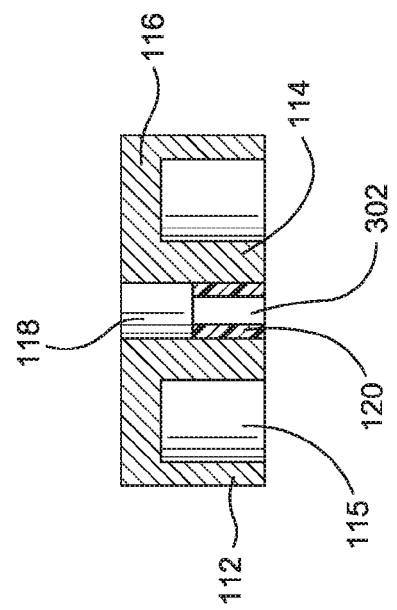
FIG. 3B
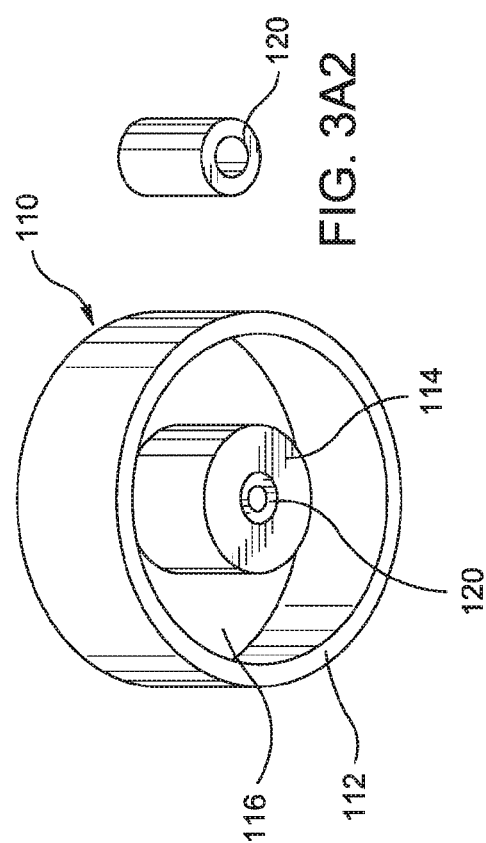
FIG. 3A2
FIG. 3A1

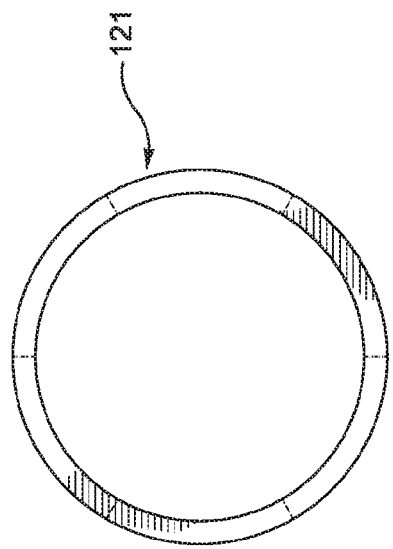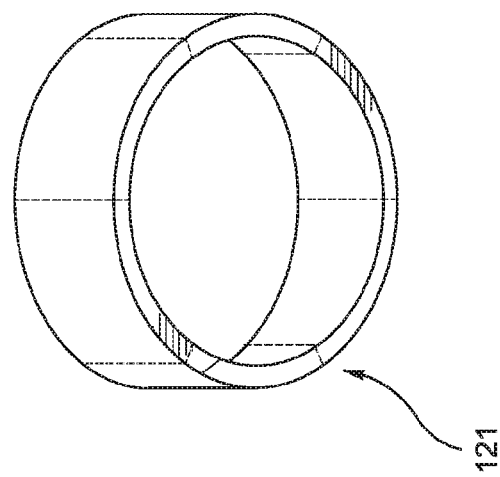

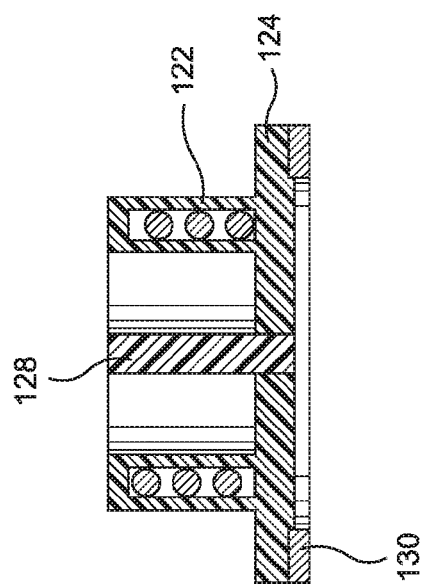
FIG. 5B
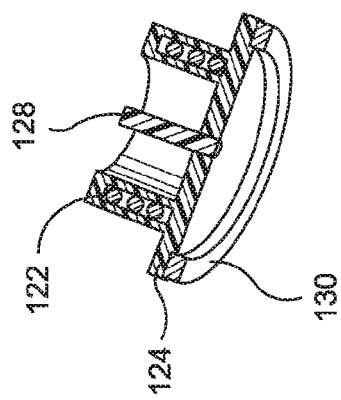
FIG. 5A2
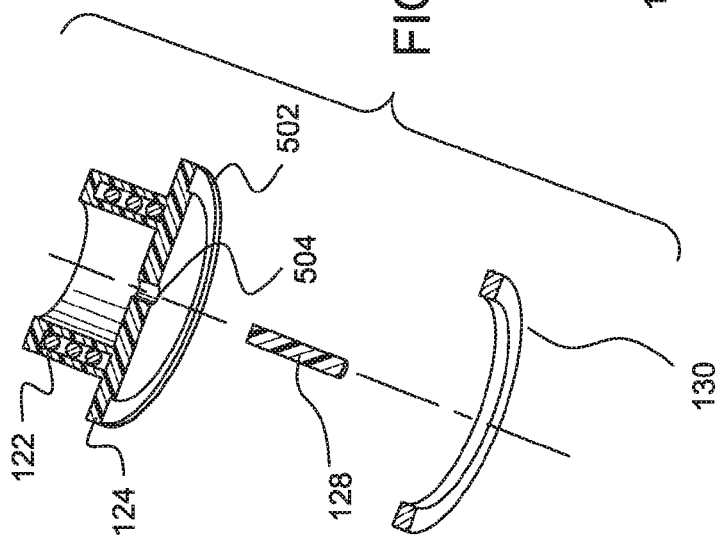
FIG. 5A1

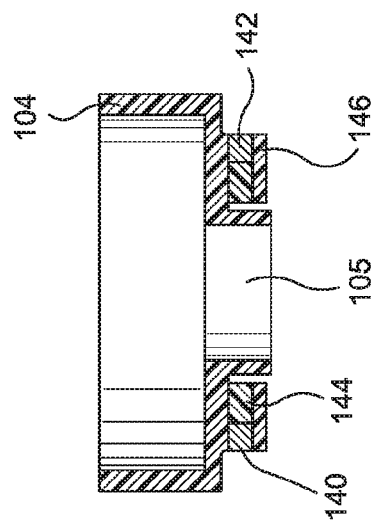
FIG. 6A1
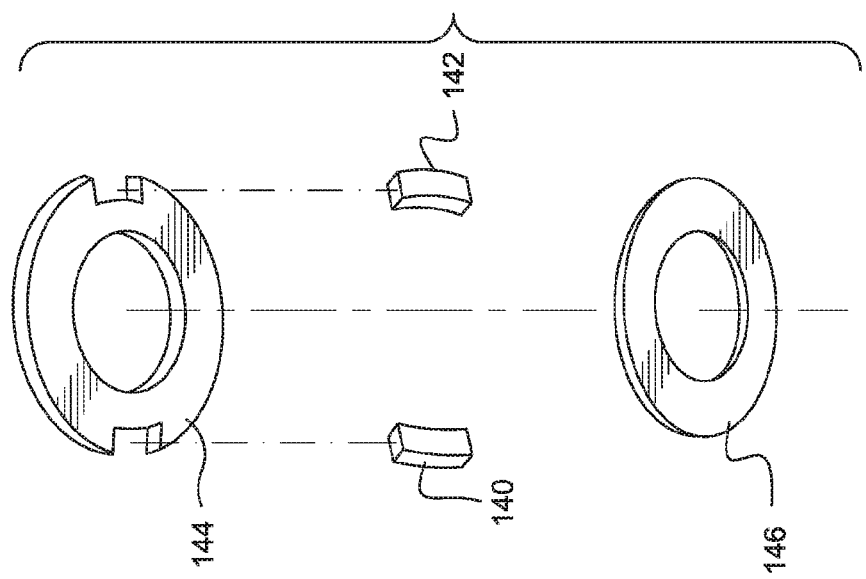
FIG. 6A2
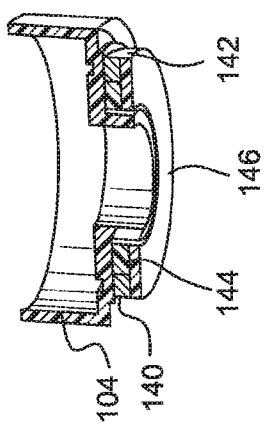
FIG. 6B

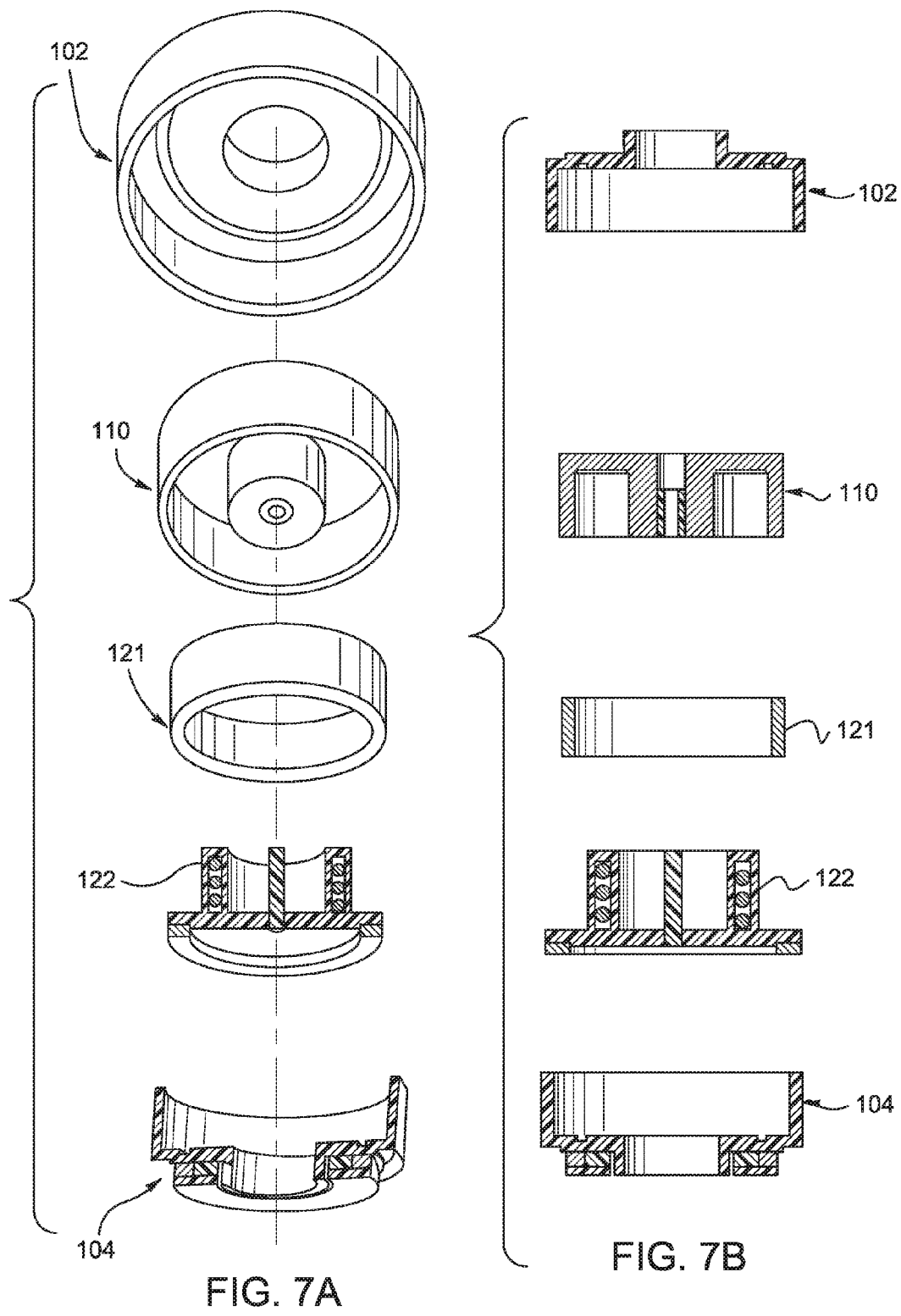

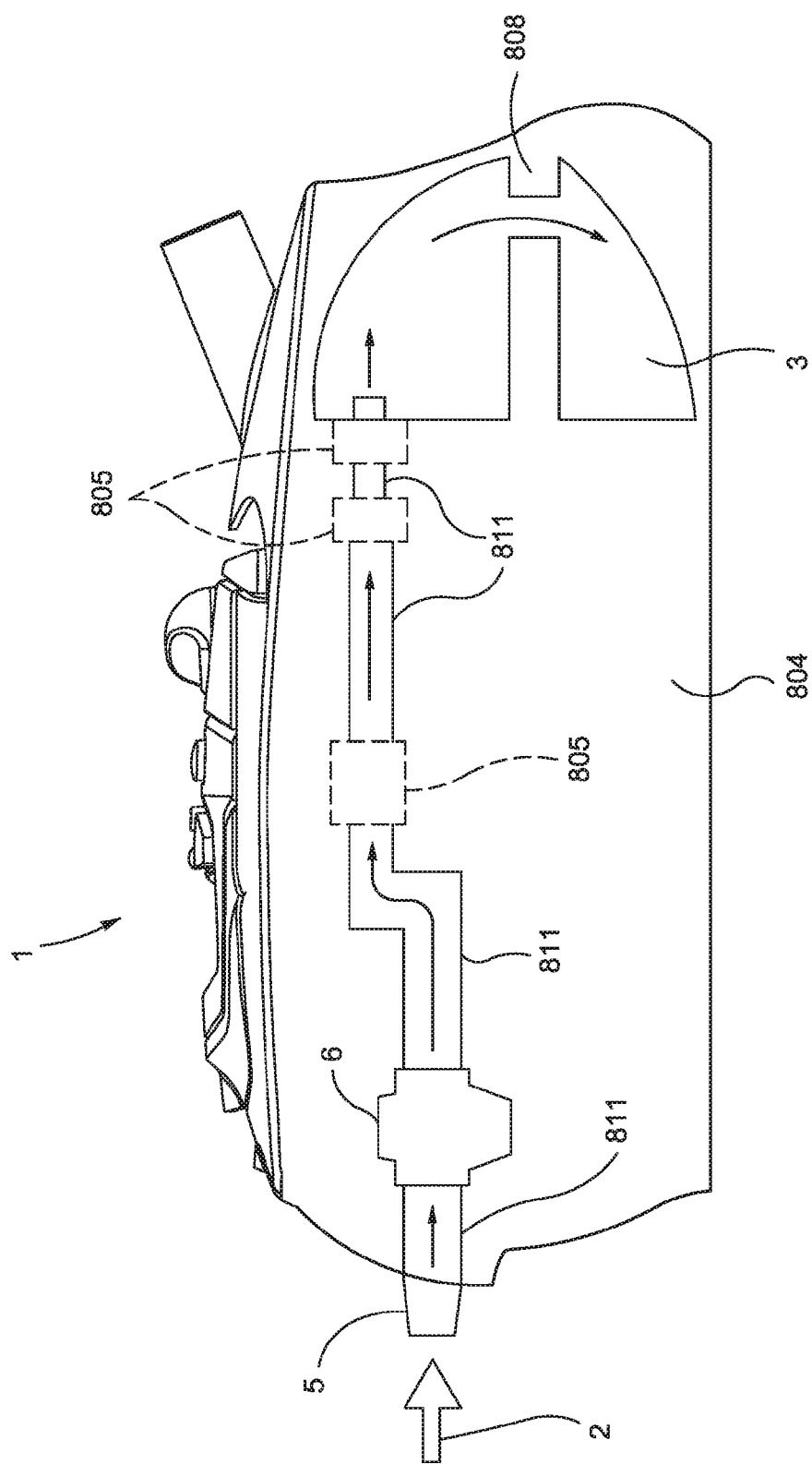

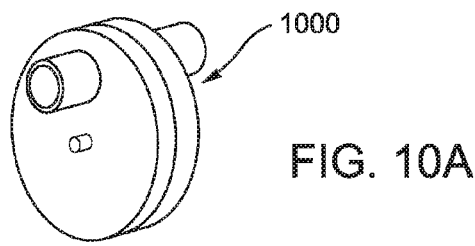
FIG. 10A
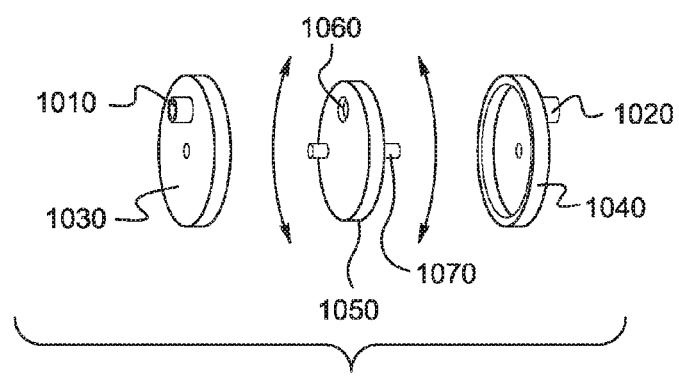
FIG. 10B
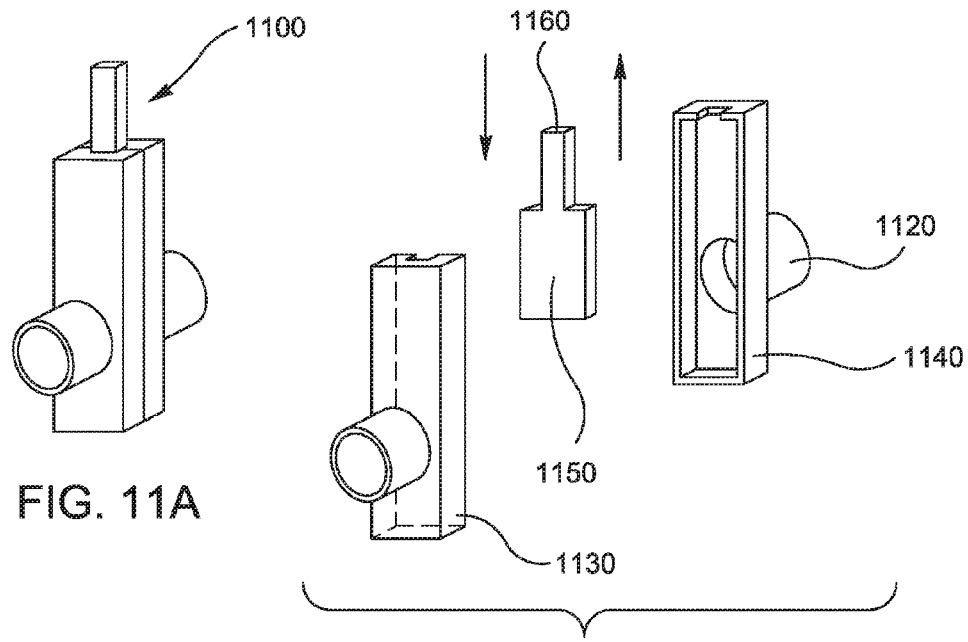
FIG. 11A
FIG. 11B

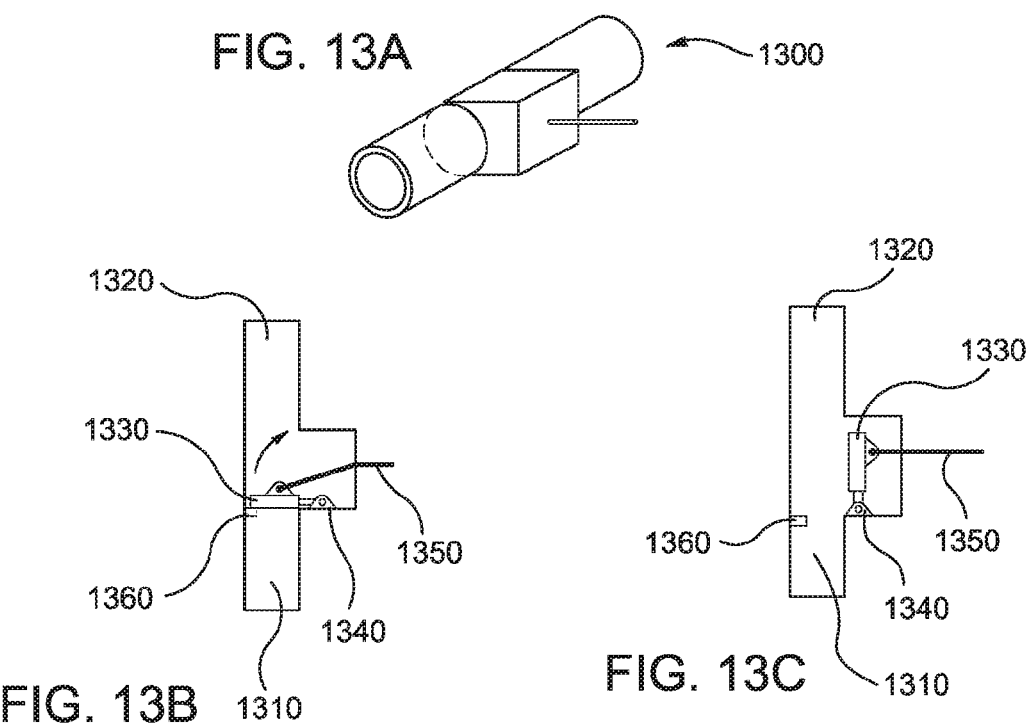
FIG. 13A
FIG. 13B
FIG. 13C
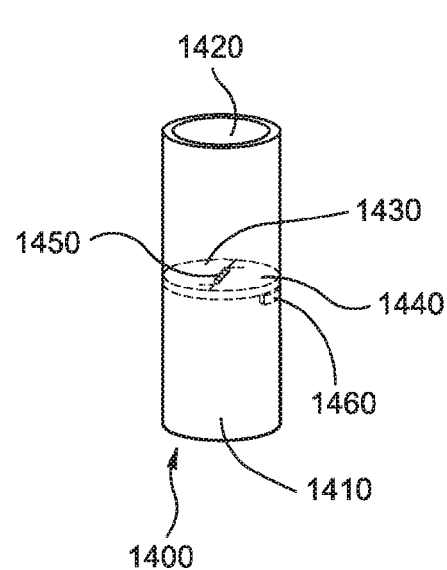
FIG. 14A
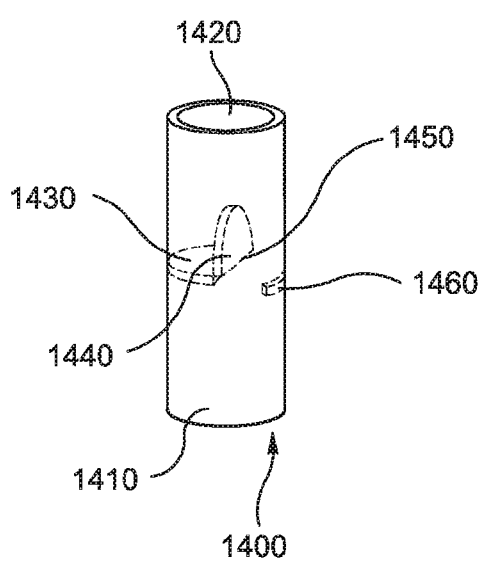
FIG. 14B
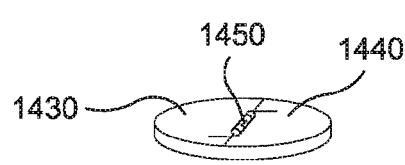
FIG. 14C

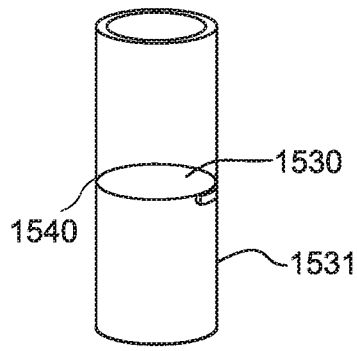
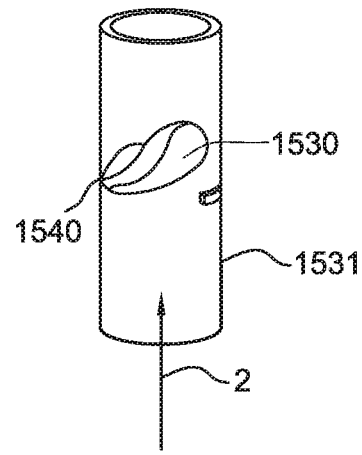
FIG. 15A  FIG. 15B
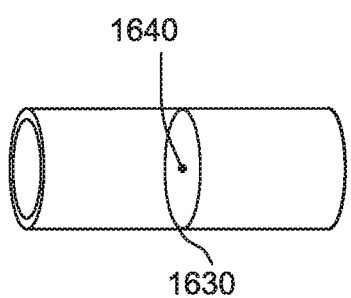
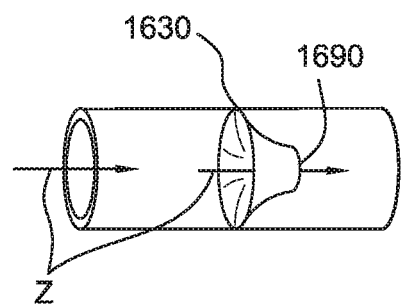
FIG. 16A  FIG. 16B

METHOD AND APPARATUS FOR BACKSPILL PREVENTION

CROSS REFERENCE TO APPLICATIONS

This application is a division of U.S. patent application Ser. No. 12/285,342, filed Oct. 2, 2008, allowed, which claims the benefit of U.S. Provisional Patent No. 60/996,159, filed Nov. 5, 2007, each of which is incorporated herein by reference in its entirety.

TECHNOLOGICAL FIELD

The technology herein relates to a method and apparatus for backspill prevention. More particularly, the technology herein relates to a method and apparatus for positive airway pressure (PAP) device backspill prevention using a controlled backspill prevention apparatus.

BACKGROUND AND SUMMARY

PAP devices are designed for portable use and aid in the treatment of sleep apnea. Using pressurized air delivered through, for example, a face-mask, they force a patient's airways open, allowing unobstructed breathing during sleep.

In addition to delivering pressurized gas into one or more of the patient's airways, PAP devices can be connected to or otherwise provided to other useful accessories, such as a humidifier. The humidifier can even be included as a part of the device. For example, it can be provided in the form of a small chamber housed therein. In either case, the humidifier typically includes a supply of water (e.g., up several hundred milliliters).

While such a combination is convenient for the patient, it does suffer from some potential drawbacks. For example, the tube by which the humidified gas is provided to the patient is also in communication with the fan or blower motor, either directly or indirectly. Unfortunately, the fan or blower is typically not waterproof, and if too much moisture or water contacts the fan or blower motor, some or all of the PAP device can be destroyed and/or a short circuit can occur. Since the humidifier and motor often communicate through the same air passageway, this backspill is a regularly occurring problem.

In normal, intended use, such arrangements do not present a problem, as the device is designed such that water from the humidifier chamber does not flow back down the air passageway and into the fan or blower housing. Problems arise, for example, when the device is turned off and being transported from one place to another. The person carrying the machine may not even be aware of a need to keep it oriented in a certain position, or they may not be aware that water has a potential to leak or splash from the humidifier into the fan motor. If the machine is improperly or carelessly carried and backspill water reaches the fan motor, when the machine is next activated, the motor may short out or be destroyed entirely, resulting in a costly repair bill or perhaps the need to replace the entire device.

The exemplary illustrative non-limiting implementations herein provide a device which can be fit within a PAP device and which prevents such a backspill from occurring by sealing the air passageway when the machine is turned off for transportation.

According to one exemplary illustrative non-limiting implementation, a first magnet is housed within a chamber and has a magnetic field oriented substantially towards a hollow center thereof and an outer edge thereof. A solenoid interfaces with the hollow center of the magnet and is further provided with a backspill stop that includes some amount of magnetically attractable material. One or more second magnets are also provided to the housing, having magnetic fields directed towards the backspill stop. The second magnets are situated generally near the outside of an opening in the housing, and the magnets function to hold the backspill stop in place against the housing, blocking the opening. When the solenoid is activated, it interacts with the radial magnetic field of the first magnet to pull the backspill stop away from the opening as the solenoid is drawn through the magnetic field in a direction away from the opening.

In a further exemplary illustrative non-limiting implementation, the solenoid/backspill stop combination is built into a PAP or other device as part of the assembly process thereof (e.g., it is a part of the air passageway, housed in a chamber larger than the passageway that it is intended to restrict). In another exemplary illustrative non-limiting implementation, the solenoid/backspill stop combination is housed in a connecting piece that can be inserted between two passageways at a desired location.

In still another exemplary illustrative non-limiting implementation, other controllable backspill prevention mechanisms are used to block and unblock a passageway in a PAP device. These exemplary backspill prevention implementations allow air passage in a first position and block the passageway in a second position.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 1A shows an exemplary PAP device including a humidifier chamber according to an example of the present invention;

FIG. 1D shows the cross section of FIG. 1B with the exemplary solenoid backspill prevention apparatus in a closed position;

FIG. 2A shows a perspective view of a portion of an exemplary housing first portion according to an example of the present invention;

FIG. 2B shows a cross section of the housing first portion of FIG. 2A;

FIGS. 3A1 and 3A2 show a perspective view of an exemplary receiving cylinder and an exemplary linear bearing according to an example of the present invention;

FIG. 3B is a cross-sectional view of the exemplary receiving cylinder and exemplary linear bearing of FIGS. 3A1 and 3A2;

FIG. 4A shows a perspective view of an exemplary cylindrical magnet according to an example of the present invention;

FIGS. 4B and 4C show, respectively, a cross section and a top view from above of an exemplary cylindrical magnet;

FIGS. 5A1 and 5A2 show an exploded perspective cross-sectional view and cross-sectional view, respectively, of an exemplary engaging solenoid including a backspill stop, an exemplary ring of magnetically attractable material, and an exemplary guide shaft according to an example of the present invention;

FIG. 5B is an assembled view of an the exemplary engaging solenoid of FIGS. 5A1 and 5A2;

FIGS. 6A1 and 6A2 show a cross-sectional perspective view an exploded perspective view, respectively, of an exemplary housing second portion, an exemplary magnet positioning ring, exemplary magnetic material, and an exemplary retaining ring according to an example of the present invention;

FIG. 6B shows an assembled view of the exemplary housing second portion of FIGS. 6A1 and 6A2;

FIG. 7A shows a perspective view of an exploded exemplary solenoid backspill prevention apparatus according to an example of the present invention;

FIG. 7B shows a cross-sectional view of the exploded exemplary solenoid backspill prevention apparatus of FIG. 7A;

FIG. 8 is a schematic view of an exemplary solenoid backspill prevention apparatus provided to an exemplary PAP device according to an example of the present invention;

FIGS. 10A and 10B show an exemplary dial backspill prevention apparatus according to an example of the present invention;

FIGS. 11A and 11B show an exemplary slidable gate backspill prevention apparatus according to an example of the present invention;

FIGS. 13A, 13B and 13C show an exemplary hinged-gate backspill prevention apparatus according to an example of the present invention;

FIGS. 14A, 14B and 14C show an exemplary one-way hinged-gate backspill prevention apparatus according to an example of the present invention;

FIGS. 15A and 15B show an exemplary resilient flap backspill prevention apparatus according to an example of the present invention; and FIGS. 16A and 16B show an exemplary valve diaphragm backspill prevention apparatus according to an example of the present invention.

DETAILED DESCRIPTION OF ILLUSTRATED EMBODIMENTS

Figure 1C:
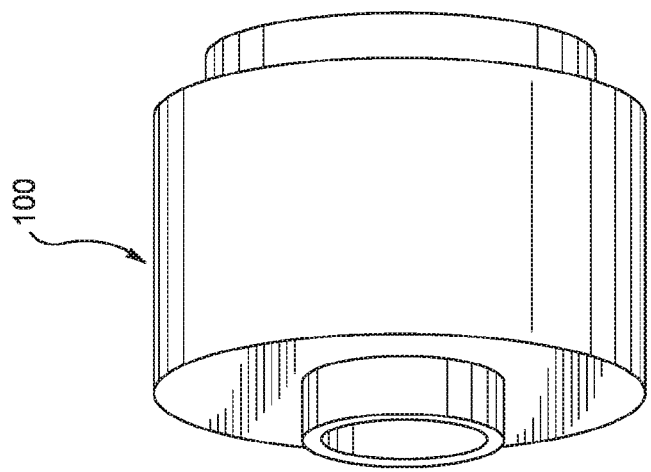
FIG. 1C is a perspective view of the exemplary solenoid backspill prevention apparatus of FIG. 1B.

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

1.0 Exemplary PAP Device

FIG. 1A shows an exemplary PAP device 1 provided with a humidifier chamber 3. When the device 1 is operated, motor 6 powers a fan to suck air 2 in through intake 5. After passing through the device 1 interior, the air 2 exits through entry connector 9 into pre-humidifier chamber 7.

The air 2 is then forced down humidifier entrance opening 11 into the humidifier chamber 3. Air pressure forces the air 2 up through exit 19.

If the PAP device is, for example, inverted, the water from humidifier chamber 3 can pour through humidifier entrance opening 11 into pre-humidifier chamber 7. This water can then pass through entry connector 9 and reach motor 6 inside the PAP device.

2.0 Exemplary Solenoid Backspill Prevention Apparatus

Figure 1B:
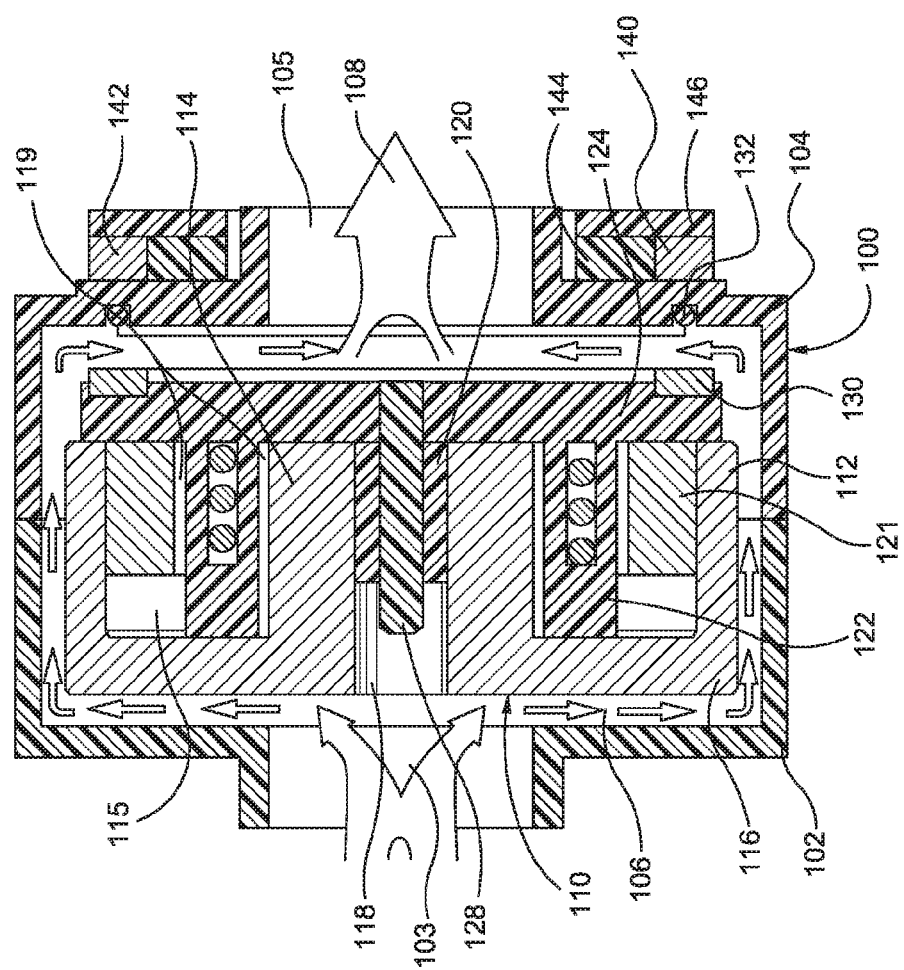
FIG. 1B shows a cross-section of an exemplary solenoid backspill prevention apparatus according to an example of the present invention.

FIG. 1B shows an exemplary solenoid backspill prevention apparatus 100 in cross-section. According to this exemplary illustrative non-limiting implementation, an apparatus housing 100 has a first portion 102 and a second portion 104. The two housing portions 102, 104 define a chamber 106 which houses much of the remaining apparatus and through which air 108 can flow. According to this implementation, each housing portion 102, 104 is provided with a respective opening 103, 105 through which air can pass into and out of the central chamber 106.

In addition to air 108 flowing through the chamber 106, in this implementation a receiving cylinder 110 is included in the apparatus 100. The cylinder has an outer wall 112 and an inner wall 114 connected by a closed end 116 and separated by hollow portion 115. According to this illustrative implementation, the closed end 116 has a guide hole 118 provided therethrough, which extends the length of the inner cylinder 114 wall. While there is a single, centrally located guide hole in this implementation, a plurality of guide holes, provided at suitable locations could also be used, or guide holes could be excluded from the apparatus entirely.

In this illustrative implementation, there is also a linear bearing 120 provided to the guide hole 118. The bearing 120 has a hollow center through which a guide shaft 128 can pass. Guide holes could also be provided without linear bearings, and the guide shafts could interface directly with the guide holes.

According to this illustrative implementation, a cylindrical first magnet 121 is arranged generally inside the hollow portion 115 of the receiving cylinder 110. The cylindrical first magnet in this implementation is shaped like a ring, and a hollow center of the magnet 121 has a greater diameter than the inner wall 114 such that a gap 119 exists between the hollow center and the inner wall 114.

In this illustrative implementation, the gap 119 is large enough to allow passage of an engaging solenoid 122. At one engaging solenoid end is a backspill stop 124. Since this backspill stop 124 will be covering the opening 105 in the housing when the apparatus is closed, it has a diameter greater than that of the opening 105. The backspill stop is also provided with at least one piece of magnetically attractable material 130, which in this implementation is in a ring shape. The magnetically attractable material 130 shape is not critical, but at least some portion of the magnetically attractable material 130 should be in a position such that it is attracted to magnets 140, 142 when the solenoid is not powered. Magnets 140, 142 could also be provided as a single magnetic ring.

Additionally, in this exemplary implementation, the backspill stop 124 has the guide shaft 128 mounted in the center thereof that interfaces with the linear bearing 120.

According to this illustrative implementation, an o-ring 132 is seated opposite the backspill stop 124 and surrounds the opening 105 in the second housing portion 104. While not necessary, the o-ring 132 can be provided to help create a tight seal when the backspill stop 124 is in a closed position.

In this implementation, the two magnets 140, 142 are positioned on either side of the opening 105 and held in place by a magnet positioning ring 144 and a retaining ring 146. The magnets are arranged such that their magnetic field creates a pull on the magnetically attractable material 130. This pull is great enough to pull the backspill stop 124 into sealing contact with the o-ring 132 when the solenoid is not powered, thus sealing off the opening 105 from backspill of water. When the solenoid is powered, however, it creates a stronger pull away from the opening 105 than that of the magnets 140, 142 and pulls the backspill stop 124 away from the o-ring 132 allowing air to again pass through the opening 105.

According to one implementation, the solenoid is powered when the PAP device is powered, such that as long as the PAP device is powered, the solenoid holds the backspill stop open. Other configurations are contemplated as well. For example, the solenoid could be placed in the position shown in the figures, but only be powerable in the absence of water in the vicinity of the backspill stop. Water detection can be performed by a number of known methods, such as providing a plurality of contacts to the passageway and detecting if a connection between any of the contacts is made (which would occur in the presence of, for example, water).

FIG. 1C shows a perspective view of an assembled exemplary solenoid backspill prevention apparatus 100. In this exemplary illustrative non-limiting implementation, the apparatus is provided as a connecting piece which can be inserted between two passageways, such as two lengths of tubing. It is also contemplated that the solenoid backspill prevention apparatus may be provided in a variety of fashions, such as being included in the assembly of a device (as opposed to being a removable piece), being included as a part of a larger removable piece, etc.

FIG. 1D shows the solenoid backspill prevention apparatus of FIG. 1B. In this exemplary illustration, the backspill stop 124 has moved into a sealing arrangement with O-ring 132. This arrangement prevents air and water from moving past the backspill stop 124.

2.0.1 Exemplary First Housing Portion

FIGS. 2A and 2B show perspective and cross-sectional views of an exemplary first housing portion 102. In this illustrative exemplary non-limiting implementation, the first housing portion comprises a first cylindrical wall 202 having a partially closed end and an open end. The partial closure is created by disk 204 having an opening 103 in the center thereof. The opening 103 is further ringed by a second cylindrical wall 206. Although the shapes of the exemplary implementation are described in the examples as being cylindrical, they could be made in any shape suitable for a particular application.

2.0.2 Exemplary Receiving Cylinder

FIGS. 3A1, 3A2 and 3B show different views of an exemplary receiving cylinder 110. The exemplary receiving cylinder has a plurality of cylindrical walls 112, 114 provided thereto and joined by a disk 116. In this exemplary illustrative non-limiting implementation, the inner cylindrical wall 114 has an additional bore down the center thereof and passing through the disk 116, creating guide hole 118.

According to this illustrative implementation, the guide hole 118 is further provided with linear bearing 120. The linear bearing 120 has a hollow core 302 to allow insertion of the guide shaft (128, FIGS. 5A1, 5A2 and 5B) provided to an engaging solenoid.

Between the cylindrical walls 112, 114 is a hollow area 115 adapted for receiving both a cylindrical magnet (121, FIGS. 4A and 4B) and an engaging solenoid (122, FIGS. 5A1, 5A2 and 5B). When the solenoid activates, it creates a magnetic field, which interfaces with a radial magnetic field of the cylindrical magnet, drawing a backspill stop portion (124, FIGS. 5A1, 5A2 and 5B) of an engaging solenoid, provided with a magnetically attractable material (130, FIGS. 5A1, 5A2 and 5B), away from an opening. The interaction between the solenoid field and the radial field also pushes the engaging solenoid guide shaft to upwards into the guide hole 118. In this way, the engaging solenoid is kept in alignment with the receiving cylinder so that the solenoid backspill prevention apparatus can continue to operate properly.

While the configuration shown functions to keep the engaging solenoid and the receiving cylinder aligned, a variety of configurations and shapes performing the same function can be implemented without departing from the scope of the present invention. The particular configuration shown herein is for exemplary purposes only.

2.0.3 Exemplary Cylindrical Magnet

FIGS. 4A and 4B show a plurality of views of an exemplary cylindrical first magnet 121. In this exemplary illustrative non-limiting implementation, the solenoid is generally ring shaped and has an outer diameter that is smaller than an inner diameter of the receiving piece's outer cylinder wall 112. This allows the magnet 121 to fit within the hollow portion 115 of the receiving cylinder.

According to this implementation, the cylindrical magnet 121 is formed of six pieces of magnet, fused together, having alternating field orientation. The fields of the magnets are further aligned radially, so that the field is focused at least towards the center of the cylinder. When a solenoid provided at least partially within the cylinder is activated, the field generated by the solenoid causes the solenoid to be drawn through the center of the cylinder as the solenoid field interacts with the radial field. The pieces of magnet, which can also be more or less than six, as is suitable for a particular application, can also be pressed together, glued together, or held together by any other suitable means.

According to this implementation, the force generated by the solenoid being drawn through the radial magnetic field must be great enough to overcome a magnetic force applied to a piece of magnetically attractable material (130, FIGS. 5A1, 5A2 and 5B) by second magnets (140, 142, FIGS. 6A1, 6A2 and 6B).

The amount of force that the solenoid must generate is at least partially dependent on the strength of the magnets 140,142 opposite the solenoid. For example, the stronger the magnets, the more force the solenoid will have to generate, since the magnetic force generated to be overcome by the solenoid will be greater.

2.0.4 Exemplary Engaging Solenoid

FIGS. 5A1, 5A2 and 5B show views of an exemplary engaging solenoid 122. According to this exemplary illustrative non-limiting implementation the wall of the solenoid 122 serves as a guide to keep the engaging solenoid 122 properly aligned. Resultantly, it is thin enough and has the appropriate diameter to fit between an inner diameter of the cylindrical magnet 121 and outer diameter of the receiving cylinder's inner cylindrical wall 114. This configuration allows the engaging solenoid to move freely while maintaining its alignment.

According to this exemplary implementation, the solenoid comprises a wound piece of wire wrapped about a cylinder and creating an electromagnet. Some parameters for an exemplary solenoid coil are given below for illustrative purposes only, and are not intended to limit the scope of the invention in any way and in fact may be varied up to ±20% of the exemplary values shown below:

| Parameter | Unit | Value |
| --- | --- | --- |
| Coil one side dimensions | mm | 65.17 |
| Filling Factor | | 0.45 |
| Current Density | A/mm$^2$ | 5.5 |
| Ampere turns | | 161.295 |
| Coil Current | A | 0.5 |
| Number of turns | | 322.59 |
| Number of turns (rounded) | | 323 |
| Average Coil Diameter, | mm | 24.3 |
| Average Turn Length, | mm | 76.341 |
| Total Wire Length | mm | 24658.0 |
| Single Wire Area | mm$^2$ | 0.091 |
| Wire Diameter, | mm | 0.340 |
| AWG | | 27.5 |
| Coil Resistance | Ohm | 4.676 |
| Coil Voltage | V | 2.338 |
| Coil Power at Steady State | W | 1.169 |

In this exemplary implementation, a backspill stop 124 is provided at one end of the engaging solenoid. This backspill stop 124 acts as the valve that seals off the passageway 105, and has a greater diameter than the passageway 105. At least one piece of magnetically attractable material 130 is also provided to the backspill stop.

According to this exemplary implementation, the piece of magnetically attractable material is a ring 130, however it could be several pieces, a solid disk, etc. The ring 130 is positioned such that it can be attracted by a field generated by the second magnet(s) 140, 142. An exemplary ring 130 positioning places it within a groove 502 cut in the bottom of the disk. The groove 502 is cut to have a diameter that places at least portions of the groove in lateral alignment with the magnetic material 140,142 when the apparatus is assembled. Regardless of the form in which the magnetically attractable material is provided, the only limits on its positioning are that it should be attractable by magnetic fields from the magnetic material 140, 142.

Additionally, in this implementation the magnetically attractable material 130 is shown as being provided on a first face of the backspill stop 124, but the material 130 could also be embedded in the backspill stop 124, the backspill stop 124 could be comprised of the material 130, or the material 130 could be on a different face of the backspill stop 124.

In this exemplary implementation, the backspill stop 124 also has a central hole 504 provided therein into which a guide shaft 128 can be placed. The guide shaft 128 is designed to interface with a linear bearing 120, although it can additionally simply interface with a guide hole 118. Also, the shaft need not be centered, nor is it a requirement that there be only one shaft. If a plurality of guide holes are present then a plurality of guide shafts may be present. Conversely, if no guide holes are present, then the guide shafts may be excluded altogether. In this implementation, the guide shaft 128 helps to keep the engaging solenoid 122 in proper alignment to maintain backspill stop functionality.

2.0.5 Exemplary Second Housing Portion

FIGS. 6A1, 6A2 and 6B show views of an exemplary second portion of a solenoid backspill prevention housing 104 having an opening 105 therein. Two magnets 140, 142 are provided at the general outside diameter of the opening 105, although in this implementation there is a magnet positioning ring 144 interposed between the opening 105 and the magnets 140, 142. A retaining ring 146 holds the magnets and the positioning ring in position against the second housing portion 104, and may further be part of the magnetic circuit. The retaining ring is made from soft magnetic material having high permeability in one exemplary implementation.

The magnets 140, 142 are positioned such that they are in general lateral alignment with at least a portion of the magnetically attractable material 130. Additionally the magnets should be strong enough to pull the engaging cylinder 122, including the backspill stop 124 and magnetically attractable material 130 into a closed position from an open position. This generally means that the larger the gap between the magnets 140, 142 and the attractable material 130, the stronger the magnets will have to be. The magnets might also need to be strong enough to hold the backspill stop 124 in position with some amount of pressure being applied to the backspill stop from the side of the opening 105. For example, if the solenoid backspill prevention apparatus was implemented in a PAP device, then if the patient tilted the device improperly and spilled water down the air passageway while the solenoid was turned off, the magnets 140, 142 might need to be strong enough to hold the backspill stop 124 in a closed position against water pressure and prevent water from reaching the fan.

Further, the magnets 140 and 142 may be installed in the way that their directions of magnetization are opposite to each other in one exemplary implementation. For instance, if the surface of the magnet 140 which interfaces with the retaining ring 146 has the direction of the North Pole magnetization, the similar surface of the magnet 142 has the South Pole direction.

While an exemplary positioning of two magnets is shown for illustrative purposes, it is contemplated that a variety of positionings and one or several magnets could be used. For example, a single magnet could be placed directly against the outer wall of the opening 105 or three or four magnets could be spaced periodically therearound. Any configuration rendering the backspill stop operational can be used.

2.1 Exemplary Solenoid Apparatus (Exploded View)

FIGS. 7A and 7B show exploded views of an exemplary solenoid backspill prevention apparatus. Outer portions 102, 104 form the housing for the apparatus, holding receiving cylinder 110, cylindrical magnet 121, and engaging solenoid 122 thereinside. Receiving cylinder 110 and engaging solenoid 122 align and are provided with cylindrical magnet 121 interposed therebetween.

3.0 Exemplary Solenoid Backspill Prevention Apparatus Provided to a PAP Device

FIG. 8 shows an exemplary schematic of an exemplary solenoid backspill prevention apparatus provided to an exemplary PAP device 1. Air 2 enters through intake 5 and moves into passageway 811. The air 2 is sucked in by motor 6 powering a fan and then forced further down passageway 811.

The motor 6 is not protected from water and can be damaged if water comes in contact with it, so the solenoid backspill prevention apparatus 805 should be positioned between the motor 6 and a humidifier tank 3.

The solenoid backspill prevention apparatus 805 may be placed within the PAP device housing 804, between the PAP device housing 804 and the humidifier housing 808, or within the humidifier housing 808. In any of those placements, the apparatus 805 can prevent water from escaping from the tank 3 and moving back into the passageway 811 to contact the motor 6.

Additionally, the PAP device can be provided with a button, switch or similar mechanism that allows a person carrying the PAP device to indicate that the device is being transported. For example, upon activation of the transport indicator, the backspill prevention apparatus could move to a sealing arrangement (e.g. as shown in FIG. 1D), thus preventing backspill of water while the device is in transit.

Alternatively, or additionally, the PAP device could be provided with one or more movement or orientation sensors, such as a mercury switch. The sensor(s) could be arranged so that, in certain orientations, the switch(es) are triggered. For example, if the device was inverted, turned sideways, or placed in any other orientation in which water was likely to leak out of the humidifier chamber, the switch(es) could cause the backspill prevention apparatus to seal the air passageway.

The PAP device could also be provided with moisture sensors that sense the presence of any water in the passageway in the region of the backspill prevention apparatus. Alternatively, these sensors could be configured such that a minimum amount of water must be present in order to trigger the moisture sensors. Upon detection of any or a specified minimum amount of water, the sensors could cause the backspill prevention apparatus to seal the air passageway.

4.0 Exemplary Alternative Solenoid Backspin Prevention Apparatus

Although a specific solenoid backspill prevention apparatus has been presented herein for exemplary purposes, it is contemplated that a variety of different configurations of solenoid backspill prevention apparatus could be used to block/unblock a passageway of a PAP device. FIGS. 9A-9E present a non-exhaustive set of examples of further solenoid backspill prevention apparatus which could perform substantially the same functionality.

Figure 9A:
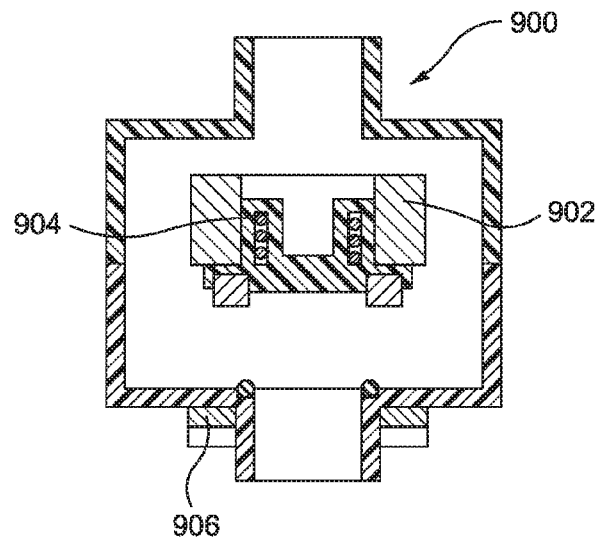
FIGS. 9A-E show various exemplary implementations of additional solenoid backspill prevention apparatuses according to examples of the present invention.

The solenoid backspill prevention apparatus 900 in FIG. 9A includes a backspill stop similar to the one shown in FIGS. 1-7, except here an inner cylinder of magnet 902 receives engaging solenoid 904. There is no receiving cylinder presented in this embodiment, rather the cylinder of engaging solenoid 904 fits within the center diameter of magnet 902. Magnets 906 are provided in generally the same place as the magnets 140, 142 from FIGS. 7A and 7B.

Figure 9B:
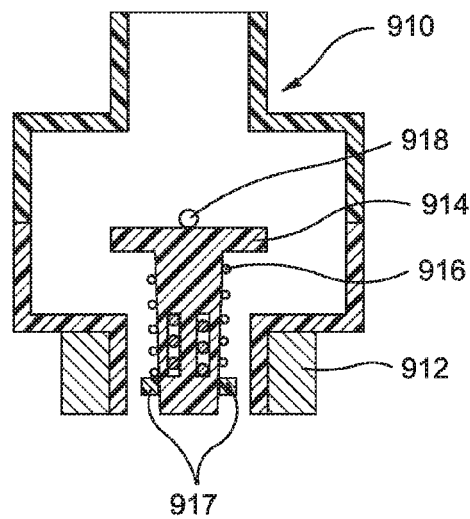

Another solenoid backspill prevention apparatus 910 in FIG. 9B uses a similar engaging solenoid 914, but no oppositional magnets. Instead, the magnet 912 is provided to the outer housing portion and, when the solenoid 914 is powered, a housing opening is sealed. When the solenoid 914 is not powered, a spring 916 biases the engaging solenoid into an open position and unseals the opening. Supports 917 hold the engaging solenoid and spring in place and stop 918 prevents the engaging solenoid from moving past a predetermined position.

Figure 9C:
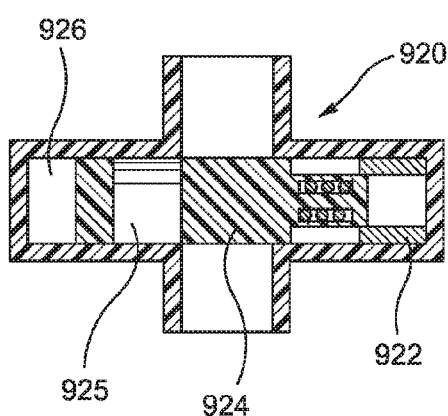
Figure 9D:
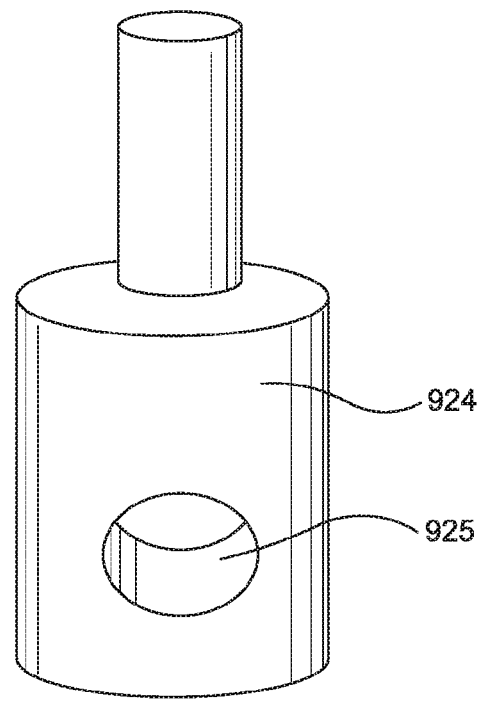

Still a further solenoid backspill prevention apparatus 920 in FIGS. 9C and 9D has an entirely different engaging solenoid 924, provided with a passageway 925 therethrough. Solenoid 924, when powered, interfaces with magnet 922 to pull the engaging solenoid into a position such that passageway 925 aligns with openings in the housing, allowing passage therethrough. When the solenoid is not powered, magnet 926 pulls the engaging solenoid 925 into a position such that passageway 925 is no longer aligned with an opening in the housing, preventing flow therethrough.

Pieces similar to those shown in FIGS. 9C and 9D could be used to create an additional exemplary backspill prevention apparatus that does not use a solenoid. Engaging device 924 could be spun about a radial axis such that when in a first position the passageway 925 aligns with openings in the housing and when in a second position the passageway is rotated 90° from alignment, preventing passage of water therethrough. This spinning could be done through a manual control or a motorized control.

Figure 9E:
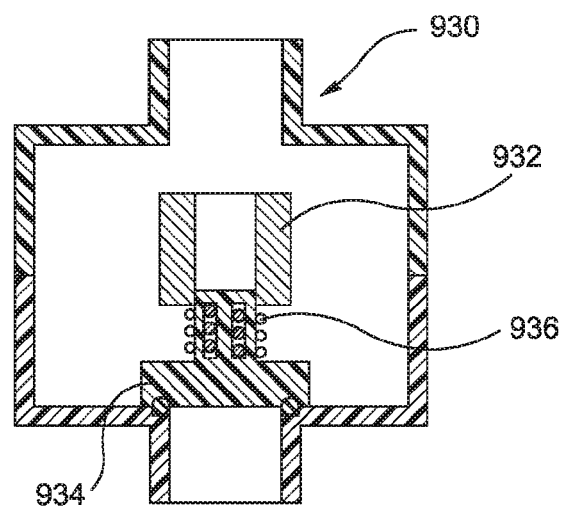

Yet another solenoid backspill prevention apparatus 930 in FIG. 9E shows a similar principal to the apparatus of FIGS. 1-7, wherein a powered engaging solenoid 934 holds a backspill stop provided to an engaging solenoid 934 in an open position. Here, however, like apparatus 900, the receiving cylinder is not included in the assembly. Additionally, instead of oppositional magnets that move the backspill stop into a closed position, a spring 936 acts to bias a backspill stop in a closed position over an opening. The force generated by the solenoid 934 interacting with the cylindrical magnet 932 must be sufficient to overcome the oppositional force of the spring to pull the engaging solenoid 934 into an open position.

While a variety of exemplary implementations have been provided in conjunction with FIGS. 9A-9E, they are intended for illustrative purposes only, and not intended to limit the scope of the invention in any way. A variety of backspill stop/solenoid combinations and configurations are possible without departing from the scope of the present invention, which is to be defined by the claims.

5.0 Additional Exemplary Backspill Prevention Apparatus for Use in a PAP Device

Additionally, while the use of a solenoid backspill prevention apparatus as a mechanism for opening and closing a passageway provided in a PAP device has been discussed in detail herein, it is appreciated that a variety of mechanisms could be employed in a PAP device to achieve similar results. A non-exhaustive set of exemplary backspill prevention apparatus is shown in FIGS. 10A-14.

FIGS. 10A and 10B show an exemplary dial mechanism 1000 that can be used to prevent the flow of undesired material down a passageway when in a first position and that can allow the passage of desired air when in a second position. Dial 1050 rotates in the directions of the arrows shown about the axis defined by seating peg 1070. Housing faces 1030, 1040 combine to create a housing for dial 1050, and openings 1010, 1020 can connect a first and second part of a passageway on either side of the dial mechanism 1000.

When the dial 1050 is rotated in one position by rotating peg 1070, dial opening 1060 is substantially aligned with openings 1010 and 1020 creating a passageway all the way through the housing. When the dial 1050 is in another position, dial opening 1060 is moved out of alignment and the connection between openings 1010 and 1020 is blocked by the dial body 1050.

Various biasing mechanisms can be used to hold the dial 1050 in a closed position when the PAP device is not powered. A motor with a locking axle running through the seating peg 1070 could be used, and the motor could turn the dial to an open position and lock it in the open position when the PAP device is powered. Or the mechanism could be manually dialed and biased by, for example, a detent arrangement. Another example of a biasing mechanism could be a spring and lock, where the spring biases the dial 1050 in a closed position and when the machine is turned on, the dial 1050 is turned against the tension in the spring and locked into an open position by a second biasing mechanism. The dial 1050 is released when the machine is turned off and the spring returns the dial 1050 to a closed position.

FIGS. 11A and 11B an exemplary slidable gate divider 1100. In this exemplary illustrative non-limiting implementation, a slidable gate 1150 is secured between two housing halves 1130, 1140. Each housing half has an opening 1110, 1120 provided therein. Through use of, for example, a sliding tab 1160, the gate 1150 can be raised and lowered across the connection between the two openings 1110, 1120. When the gate is raised, air can flow freely between the two openings, when the gate is lowered, the passageway is blocked.

As with all of the exemplary illustrative non-limiting implementations provided herein, a variety of biasing mechanisms can be used to hold the gate in an open position when the PAP device is powered and a closed position when the PAP device is not powered.

Figure 12A:
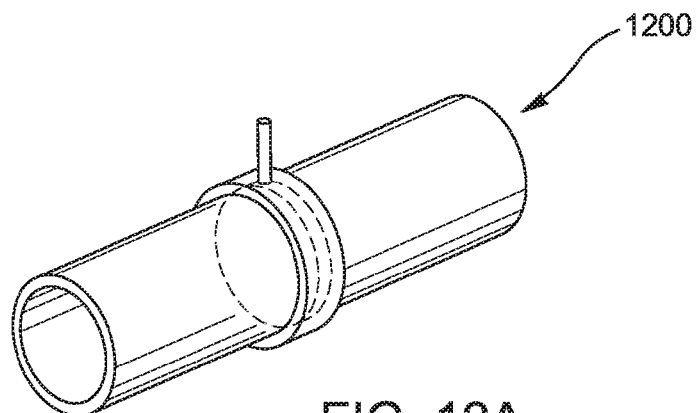
FIGS. 12A and 12B show an exemplary pivoting valve backspill prevention apparatus according to an example of the present invention.
Figure 12B:
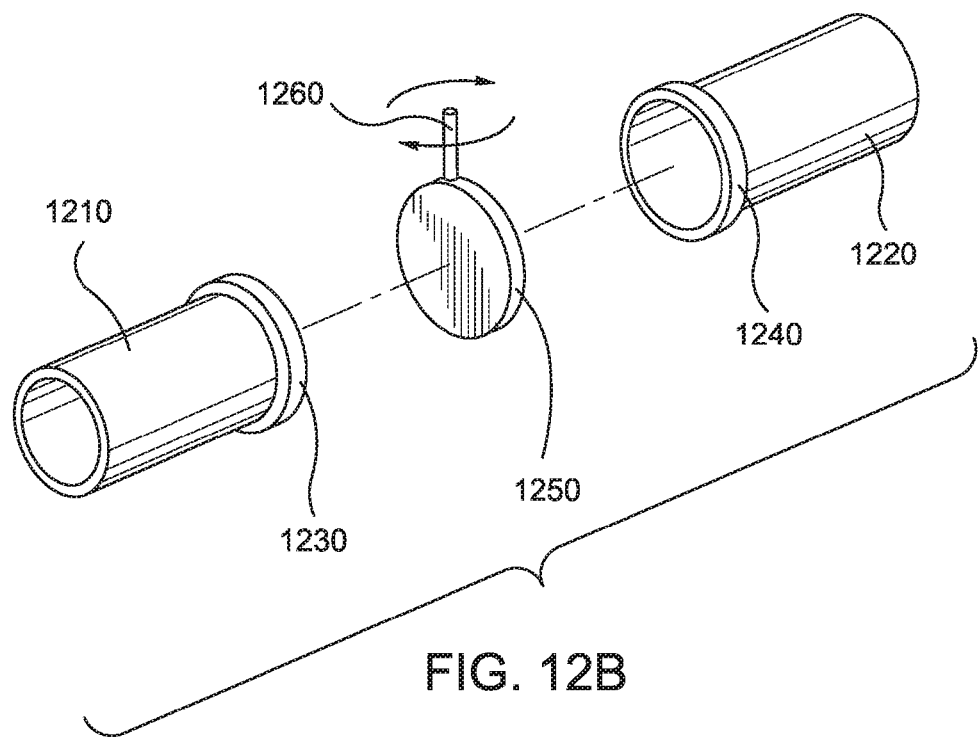

FIGS. 12A and 12B show an exemplary pivoting valve divider 1200. In this exemplary illustrative non-limiting implementation, housing portions 1230, 1240 secure a pivoting valve 1250 between them. The valve 1250 is capable of pivoting about an axis running along a valve 1250 diameter. Openings 1210, 1220 are provided in each respective housing 1230, 1240 portion to allow passage of air through the housing.

When the valve 1250 is to be closed, it is pivoted such that a valve 1250 outer edge aligns with an passageway inner edge. The pivoting can be accomplished by turning the valve controller 1260. The valve then blocks the passageway and prevents air or other material from passing therethrough. When the valve needs to be opened, it is turned 90 degrees, for example, and the passageway is then unrestricted and air can pass freely therethrough. Again, a variety of biasing mechanisms can be employed to hold the valve in an open and a closed position.

FIGS. 13A, 13B and 13C show one exemplary hinged-gate divider 1300. The cross sections show the hinged gate 1330 in open and closed positions. When the hinged gate is biased in a closed position by a suitable biasing mechanism, air cannot pass from opening 1310 to opening 1320. If, for example, a force is applied to connector 1350, the gate 1330 pivots about hinge 1340 and raises to an open position. As before, various biasing mechanisms can be used to hold the gate in open and closed positions.

In place of a hinged-gate, a simple flap could also be used as shown in FIGS. 15A and 15B. The flap 1530 could be secured to the tube 1531 at a first location 1540, and be flexible enough that air 2 against a first side would cause the flap to bend and allow air to pass by. A backstop 1560 could be provided for the first side of the flap 1530 to rest against. The flap 1530 would, when the airflow ceased, resiliently return to a circular form and rest on the backstop 1560, so that water pushing against a second side opposite the first side could not cause the flap 1530 to flex in the opposite direction.

An exemplary one-way hinged-gate divider 1400 is shown in FIGS. 14A, 14B and 14C. In this divider, two halves 1430, 1440 of a circle of material are positioned across a passageway and connected by a hinge or a living hinge. One of the halves 1430 is fixedly attached to an inner wall of the passageway while the other half 1440 can pivot about the hinge.

According to this exemplary illustrative non-limiting implementation, the biasing mechanism that holds the hinged-gate in a closed position is a spring 1450. The spring constant on the spring is low enough that air blowing into opening 1410 can push the pivoting half of the gate 1440 to an open position. When the airflow ceases, the spring will bias the pivoting gate half 1440 to a closed position against gate-stop 1460. If an improper material, such as water, enters the passageway through opening 1420, the gate-stop 1460 will prevent the hinged-gate from swinging in the other direction.

Still another possible exemplary divider implementation is shown in FIGS. 16A and 16B. This implementation includes a flexible diaphragm 1630 having a small hole 1640 in the center thereof. Air 2 pressure can cause the hole 1640 to expand and allow the air 2 to pass therethrough. When there is insufficient pressure, however, the hole 1640 contracts and blocks the passageway. Although this particular implementation may not be able to prevent all water passage, it should still provide protection against at least partial water passage towards the motor.

Although a variety of possible exemplary divider implementations have been presented herein, they are presented for illustrative purposes only and not intended to limit the scope of the invention in any way. Numerous different dividers can be used to achieve the blocking and unblocking of the passageway. Also, although blocking the passageway is generally discussed as being the divider location when the machine is turned off and unblocking the passageway is generally discussed as being the divider location when the machine is turned on, the blocking can also be designed to take place under other circumstances. For example, the blocking may occur in the presence of water in the vicinity of the divider.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A PAP device comprising:
  a blower operable to force air through at least one passageway in response to a first control signal;
  a backspill prevention apparatus provided to said at least one passageway, and
  a controller to control operation of the backspill prevention apparatus,
  wherein said backspill prevention apparatus is positionable in at least first and second positions, operable to block said passageway when in said first position and operable to unblock said passageway when in said second position, the controller being configured to determine that the PAP device is operable outside of normal operating conditions and/or is being transported and provide a second control signal to move the backspill prevention apparatus between the first position and the second position.

2. The PAP device of claim 1 wherein said backspill prevention apparatus includes a solenoid backspill prevention apparatus.

3. The PAP device of claim 2, wherein the PAP device includes a humidifier attachment and said solenoid backspill prevention apparatus is positioned between the humidifier attachment and a motor powering the blower.

4. The PAP device of claim 2, wherein the solenoid backspill prevention apparatus further includes:
 a cylindrical magnet;
 a housing including a plurality of openings;
 a solenoid provided with a backspill stop operable to obstruct at least one of said openings when in a first position, said obstruction being at least partially removed when said backspill stop is in a second position; and
 a biasing mechanism operable to bias said backspill stop into one of either said first or said second position, wherein said solenoid is operable to move said backspill stop into the other of said first or said second position, and wherein said housing houses said backspill stop and at least one of said cylindrical magnet and said biasing mechanism.

5. The PAP device of claim 4, wherein said cylindrical magnet further includes a hollow center and said solenoid further includes at least an interface portion interfaced with said hollow center.

6. The PAP device of claim 4, wherein said backspill stop has sufficient surface area on at least a first surface to obstruct at least one of said openings.

7. The PAP device of claim 4, wherein said biasing mechanism includes a spring.

8. The PAP device of claim 4, wherein said biasing mechanism includes a magnet.

9. The PAP device of claim 1 wherein said backspill prevention apparatus is a rotatable divider.

10. The PAP device of claim 1 wherein said backspill prevention apparatus is a hinged divider.

11. The PAP device of claim 1 wherein said backspill prevention apparatus is a slidable divider.

12. The PAP device of claim 1 wherein said backspill prevention apparatus is a flexible flap.

13. The PAP device of claim 1, wherein said backspill prevention apparatus is a flexible diaphragm having at least a passageway therethrough.

14. A method of opening and closing a passageway provided to a PAP device including a solenoid backspill prevention apparatus connecting a first and second portion of said passageway, comprising:
 biasing a backspill stop of a solenoid backspill prevention apparatus, including at least a solenoid in a first position;
 powering a solenoid of said solenoid backspill prevention apparatus to create a first magnetic field;
 providing a second radial magnetic field aligned with said first magnetic field;
 using an interaction between said first magnetic field and said second radial magnetic field to move said backspill stop to a second position, wherein said backspill stop obstructs an opening of said solenoid backspill prevention apparatus, thereby obstructing said passageway, when in one of either said first or said second positions.

15. The method of claim 14, wherein said biasing further includes holding said backspill stop in said first position using a spring.

16. The method of claim 14, wherein said backspill prevention apparatus includes at least a first piece of magnetically attractable material and said biasing further includes holding said backspill stop in said first position using a magnet.

17. A method for operating a PAP device having a blower to deliver pressurized gas via a passage to a patient comprising:
 providing the PAP device with a backspill prevention apparatus positioned in the passage downstream of the blower;
 generating a first control signal to control the blower;
 generating a second control signal that results in allowing for unobstructed delivery of pressurized gas in normal operating conditions;
 determining that the PAP device is operable outside of normal operating conditions and/or is being transported by using a sensor or a user input; and
 adjusting the second control signal to result in at least partially obstructing a path of the passage via the backspill prevention apparatus.

18. The method of claim 17, wherein the PAP device includes the user input and the method further includes indicating, using the at least one user input, that the PAP device is to be transported.

19. The method of claim 17, wherein the PAP includes the sensor and the method further includes sensing, using the at least one sensor, that the PAP device is operating outside of normal operating conditions.

20. The method of claim 19, wherein the sensing further includes sensing that the device is being transported.

21. The method of claim 19, wherein the sensing further includes sensing that a PAP device is not in a predesignated orientation.

22. The method of claim 21, wherein the sensing further includes sensing that a PAP device is inverted.

23. The method of claim 21, wherein the sensing further includes sensing that a PAP device is turned on a side thereof.

24. The method of claim 19, wherein the sensing further includes sensing at least a predetermined amount of water within the passage.

25. The method of claim 24, wherein the predetermined amount of water is any amount of water.

26. The method of claim 17, wherein the adjusting the second control signal includes no longer providing the second control signal.

* * * * *